US006924117B2

(12) United States Patent
Lioubin et al.

(10) Patent No.: US 6,924,117 B2
(45) Date of Patent: Aug. 2, 2005

(54) HUMAN RRP SEQUENCES AND METHODS OF USE

(75) Inventors: Mario N. Lioubin, San Mateo, CA (US); Lori Friedman, San Francisco, CA (US); Marcia Belvin, Berkeley, CA (US); Jeffery S. Larson, Burlingame, CA (US); Changyou Chen, Castro Valley, CA (US); Stephanie A. Robertson, San Francisco, CA (US); Wen Shi, San Francisco, CA (US); Jocelyn Chan, San Francisco, CA (US); Danxi Li, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 6 days.

(21) Appl. No.: 09/908,419

(22) Filed: Jul. 18, 2001

(65) Prior Publication Data

US 2002/0022029 A1 Feb. 21, 2002

Related U.S. Application Data

(60) Provisional application No. 60/219,289, filed on Jul. 19, 2000, provisional application No. 60/277,487, filed on Mar. 21, 2001, provisional application No. 60/277,471, filed on Mar. 21, 2001, and provisional application No. 60/304,863, filed on Jul. 12, 2001.

(51) Int. Cl.[7] .................. C12Q 1/68; A61K 39/395; A01N 37/18
(52) U.S. Cl. ............... 435/7.23; 424/130.1; 424/178.1; 424/94.1; 514/2
(58) Field of Search ............................ 436/500; 514/2; 424/130.1, 178.1, 94.1

(56) References Cited

PUBLICATIONS

Lewin B (Genes VI, Oxford University Press, 1997, Chapter 29, p. 847–848).*
Alberts et al. (Molecular Biology of the Cell, 3rd edition, 1994, p. 465).*
Shantz and Pegg (Int J of Biochem and Cell Biol., 1999, vol. 31, pp. 107–122).*
McClean and Hill (Eur J of Cancer, 1993, vol. 29A, pp. 2243–2248).*
Fu et al (EMBO Journal, 1996, vol. 15, pp. 4392–4401).*
Yokota, J et al (Oncogene, 1988,vol. 3, pp. 471–475).*
Savino et al (J. Cell Science 1999; 112:1889–1900).*
Seaver et al (Genetic Engineering News Aug. 1994; 14(14):10&21).*
Weiner et al (Sem. Oncol. 1999 ;26(4):41–50).*
Wasserman JD et al (Genes Dev Jul. 1, 2000;14(13):1651–63).*
Database EMBL 'Online!, Accession No. Q9NX52, Oct. 1, 2000, K. Watanabe et al.: "NEDO human cDNA sequencing project" XP002192453.

Golembo, M., et al., "The Drosophila embryonic midline is the site of Spitz processing, and induces activation of the EGF receptor in the ventral ectoderm", Development , 1996, 122:3363–3370, The Company of Biologists Limited, Great Britain.
Wasserman, J.D., et al., "A family of rhomboid–like genes: Drosophila rhomboid–1 and roughoid/rhomboid–3 cooperate to activate EFG receptor signaling", Genes & Development, 2000, 14:1651–1663, Cold Spring Harbor Laboratory Press.
Schweitzer, R., et al., "Secreted Spitz triggers the DER signaling pathway and is a limiting component in embryonic ventral ectoderm determination", Genes & Development, 1995, 9:1518–1529, Cold Spring Harbor Laboratory Press.
Duffy, J.B., et al., "Recent advances in understanding signal transduction pathways in worms and flies" Current Opinion in Cell Biology, 1996, 8:231–238, Current Biology Publishing.
Pascall, J.C., et al., "Characterization of a mammalian cDNA encoding a protein with high sequence similarity to the Drosophila regulatory protein Rhomboid" FEBS Letters, 1998, 429:337–340, Federation of European Biochemical Societies.
Pascall,J.C., "Homo sapiens mRNA for rhomboid–related protein" Genbank GI No. 3287190, Jun. 30, 1998.
NIH–MGC, "602365464F1 NIH_MGC_90 Homo sapiens cDNA clone IMAGE:4473855 5',mRNA sequence"Genbank GI No. 12762689, Feb. 13, 2001.
NIH–MGC, "602251313F1 NIH_MGC_84 Homo sapiens cDNA clone IMAGE:4343882 5', mRNA sequence" Genbank GI No. 12096415, Jan. 12, 2001.
NCI–CGAP, "xv57g07.x1 NCI_CGAP_Lu28 Homo sapiens cDNA clone IMAGE:2817276 3' similar to SW:RHOM_DROME P 20350 Rhomboid Protein ;, mRNA sequence" Genbank GI No. 6657080, Jan. 3, 2000.
Dias Neto,E., et al., "QV0–CT0225–230300–169–e09 CT0225 Homo sapiens cDNA, mRNA sequence" Genbank GI No. 7947756, May 19, 2000.
NCI–CGAP, "on76e02.s1 Soares_NFL_T_GBC_S1 Homo sapiens cDNA clone" Genbank GI No. 3117010, Jun. 23, 1998.

(Continued)

Primary Examiner—Gary Nickol
Assistant Examiner—C. Yaen
(74) Attorney, Agent, or Firm—Laleh Shayesteh Exelixis, Inc.

(57) ABSTRACT

Rhomboid Related Proteins (RRPs), involved in the EGFR signaling pathway, are provided. Transgenic, nonhuman mammals containing a transgene encoding an RRP polypeptide or a gene effecting the expression of an RRP polypeptide, along with methods of modulating the interaction of RRP proteins with their pathway members, and methods of screening for agents that modulate the interaction of an RRP polypeptide with an RRP binding target, such as RRP-specific antibodies and small molecules identified in high throughput screens, are also provided. Modulating agents identified using the methods of the invention can be used to specifically inhibit growth of tumor cells that overexpress an RRP protein.

5 Claims, No Drawings

OTHER PUBLICATIONS

NIH–MGC, "601310502F1 NIH_MGC_44 Homo sapiens cDNA clone IMAGE:3631824 5', mRNA sequence" Genbank GI No. 9339870, Jul. 21, 2000.

NCI–CGAP, "hd76f05.x1 NCI_CGAP_Lu28 Homo sapiens cDNA clone IMAGE:2915457 3' similar to TR:O75783 O75783 Rhomboid–Related Protein. ;, mRNA sequence" Genbank GI No. 7152496, Mar. 3, 2000.

Dias Neto,E., et al., "RC0–EN0025–200600–031–d10 EN0025 Homo sapiens cDNA, mRNA sequence" Genbank GI No. 11317512, Nov. 22, 2000.

Dias Neto,E., et al., "RC0–EN0025–200600–031–e08 EN0025 Homo sapiens cDNA, mRNA sequence" Genbank GI No. 11317513, Nov. 22, 2000.

Dias Neto,E., et al., "RC0–EN0025–200600–031–c01 EN0025 Homo sapiens cDNA, mRNA sequence" Genbank GI No. 11317511, Nov. 22, 2000.

NIH–MGC, "601463932F1 NIH_MGC_67 Homo sapiens cDNA clone IMAGE:3867487 5', mRNA sequence" Genbank GI No. 10199673, Oct. 20, 2000.

Adams,M.D., "EST59487 Infant brain Homo sapiens cDNA d' end, mRNA sequence" Genbank GI No. 2003992, Apr. 21, 1997.

Pascall,J.C., "rhomboid–related protein" Genbank GI No. 3287191, Jun. 30, 1998.

Watanabe,K., et al., "hypothetical protein FLJ20435" Genbank GI No. 8923409, Feb. 10, 2002.

NCBI Annotation Project, "hairy (Drosophila)–homolog" Genbank GI No. 12729522, Feb. 9, 2001.

NCBI Annotation Project, "hypothetical protein FLJ20435 " Genbank GI No. 11421817, Nov. 16, 2000.

* cited by examiner

HUMAN RRP SEQUENCES AND METHODS OF USE

REFERENCE TO RELATED APPLICATIONS

This application claims priority to U.S. provisional patent applications 60/219,289 filed Jul. 19, 2000, 60/277,487 filed Mar. 21, 2001, 60/277,471 filed Mar. 21, 2001, and application No. 60/304,863, entitled "Human RRP Sequences and Methods of Use" filed Jul. 12, 2001, the contents of which are hereby incorporated in their entirety.

BACKGROUND OF THE INVENTION

Signal transduction pathways are made up of growth factors, their receptors, upstream regulators of the growth factors, and downstream intracellular kinase networks. These pathways regulate many cellular processes, including proliferation, and appear to play a key role in oncogenesis.

The epidermal growth factor receptor (EGFR) and its pathway members are among the most widely explored signaling pathways. Signaling through this pathway elicits diverse biological responses whose manifestations can include mitogenesis or apoptosis, enhanced cell motility, protein secretion, and differentiation or dedifferentiation. Up-regulated EGFR signaling has been implicated in organ morphogenesis, maintenance and repair, and is correlated with invasion and metastasis of many types of tumors. Thus, EGFR and its pathway signaling members are targets for therapeutic intervention in wound repair and cancer.

Signal transduction pathways, such as the EGFR pathway, are evolutionarily conserved among species as distant as the worm *Caenorhabditis elegans*, the fruit fly *Drosophila melanogaster*, and vertebrates (Duffy J B, and Perrimon N, Curr. Opin. Cell Biol. (1996) 8:231–238). In fact, ligands for the *Drosophila* EGFR (DER), known as Spitz (Rutledge B, et al, Genes Dev. (1992) 6:1503–1517) and Gurken (Neuman-Silberberg F S, and Schupbach T, Cell (1993) 75:165–174), are both similar to TGFα (transforming growth factor alpha), the ligand for the vertebrate EGFR (Massaque J, J Biol Chem. (1990) 265:21393–21396). The rhomboid gene, which encodes a transmembrane protein, is another upstream member of this pathway (Bier E., et al., Genes Dev. (1990) 4:190–203). In *Drosophila*, rhomboid protein transforms Spitz from a membrane-bound to a secreted form, and thus triggers and upregulates the DER signaling pathway (Wasserman J D et al, Genes Devel (2000) 14:1651–1663). DNA sequences related to rhomboid have been identified in *C. elegans* (Wasserman J D, and Freeman M, Trends Cell Biol (1997) 7:431–436), and in mammals (Pascall J C, and Brown K D, FEBS letters (1998) 429:337–340; human: GI#3287191 and GI#7020534, among others; rat: GI#3297936; ), suggesting that rhomboid function may be evolutionarily conserved. Modulating signal transduction pathway activity involved in tumor growth and development is essential in understanding the development of many cancers, and eventually, for the treatment of cancer.

The ability to screen or manipulate the genomes of model organisms such as *Drosophila* provides a powerful means to analyze biochemical processes that, due to significant evolutionary conservation, have direct relevance to more complex vertebrate organisms. Due to high level of gene and pathway conservation, the strong similarity of cellular processes, and the functional conservation of genes between *Drosophila* and mammals, identification of novel genes involved in particular pathways and their functions in flies can directly contribute to the understanding of the correlative pathways and methods of modulating them in mammals (Mechler B M et al., 1985 EMBO J 4:1551–1557; Gateff E. 1982 Adv. Cancer Res. 37: 33–74; Watson K L., et al., 1994 J Cell Sci. 18: 19–33; Miklos G L, and Rubin G M. 1996 Cell 86:521–529; Wassarman D A, et al., 1995 Curr Opin Gen Dev 5: 44–50; Booth D R. 1999 Cancer Metastasis Rev. 18: 261–284). For example, a genetic screen can be carried out in *Drosophila* in which a gene of interest is overexpressed, resulting in a visible phenotype; a cross is made with flies having mutations in other genes; and progeny are identified that have an enhancement or reduction of the original overexpression phenotype, indicating that the mutated gene is a "modifier" involved in the same or overlapping pathway as the gene of interest (Rorth P., et al., Development (1998) 125:1049–1057; WO0015843). When the gene of interest is an ortholog of a human gene implicated in a disease pathway, such as a tumor suppressor gene or oncogene, modifier genes can be identified that may be attractive candidate targets for novel therapeutics.

SUMMARY OF THE INVENTION

The present invention provides novel compound targets that are members of the Rhomboid class of proteins, hereinafter referred to as Rhomboid Related Proteins (RRP), and more specifically RRP1, RRP2, and RRP3, and are involved in the EGFR signaling pathway. The invention provides isolated nucleic acid molecules that comprise nucleic acid sequences encoding RRP protein as well as fragments and derivatives thereof. Vectors and host cells comprising the RRP nucleic acid molecules are also described.

The invention provides transgenic, nonhuman mammals containing a transgene encoding a RRP polypeptide or a gene effecting the expression of a RRP polypeptide. Such transgenic nonhuman mammals are particularly useful as in vivo test systems for studying the effects of introducing a RRP polypeptide, and regulating the expression of a RRP polypeptide (e.g., through the introduction of additional genes, antisense nucleic acids, etc).

The present invention further provides methods of modulating the interaction of RRP proteins with their pathway members. The present invention also provides methods of specifically inhibiting growth of tumor cells that overexpress RRP gene products. The invention provides methods of screening for agents that modulate the interaction of an RRP polypeptide with an RRP binding target.

Modulating agents identified using the methods can be used to specifically inhibit growth of tumor cells that overexpress an RRP protein. Preferred modulating agents include RRP-specific antibodies and small molecules identified in high throughput screens.

DETAILED DESCRIPTION OF THE INVENTION

An overexpression screen was carried out in *Drosophila* to identify genes that interact with the cyclin dependent kinase inhibitor, p21 (Bourne H R, et al., Nature (1990) 348(6297):125–132; Marshall C J, Trends Genet (1991) 7(3):91–95). *Drosophila* Rhomboid was identified as a modifier of the p21 pathway. Accordingly, vertebrate orthologs of *Drosophila* Rhomboid, preferably human orthologs, hereinafter referred to as Rhomboid Related Proteins (RRP), and in more specific embodiments, RRP1, RRP2, and RRP3, are attractive drug targets for the treatment of pathologies associated with a defective p21 signaling pathway, such as cancer.

Rhomboid Related Proteins (RRPs) are a family of integral membrane proteins that contain five or more transmembrane domains and three strongly conserved histidine residues in the putative transmembrane regions. Rhomboid domains of RRPs can be identified using the PFAM program (PFAM 01694; Bateman A., et al., Nucleic Acids Res, 1999, 27:260–2; http://pfam.wust1.edu). Sequences related to RRP DNA (RRP1: SEQ ID NO:1, RRP2: SEQ ID NO:3, and RRP3: SEQID NO:5) and protein (RRP1: SEQ ID NO:2, and RRP2: SEQ ID NO: 4) are available in the public databases (for RRP1: cDNA: GI#3287190; proteins GI#3287191; for RRP2: cDNAs: Unigene Hs1969735, GI#s: 12762689, 12096415, 6657080, 7947756, 3117010, 9339870, 7152496, 11317512, 11317513, and 11317511; proteins: GI#s:8923409, 12719522, and 11421817; for RRP3: cDNA: GI#10199673 and GI#2003992). RRP DNA sequences encode transmembrane proteins. The extracellular or intracellular domains of RRP1 protein (SEQ ID NO:2) are located approximately at amino acid residues 1–195, 217–265, 281–283, 305–307, 329–372, 393–403, and 424–438. The extracellular or intracellular domains of RRP2 protein (SEQ ID NO:4) are located approximately at amino acid residues 1–70, 92–132, 154–158, 180–182, 204–207, 229–247, 269–277, and 299–303. The extracellular or intracellular domains of RRP3 protein (SEQ ID NO:6) are located approximately at amino acid residues 1–117, 139–183, 205–207, 229–231, 253–296, 318–325, and 347–362. PFAM database (Bateman A et al, supra) search results for RRPs locate their rhomboid domains approximately at amino acid residues 239–396 for RRP1, 114–269 for RRP2, and 163–320 for RRP3.

The method of this invention is useful in the therapy of malignant or benign tumors of mammals that overexpress RRP gene products. Results from SAGE (serial analysis of gene expression) indicate overexpression of human RRP1 genes in cancers of the brain, breast, and colon; overexpression of human RRP2 gene in cancers of the pancreas and mesothelium (linings of the abdominal and pleural cavity); and overexpression of human RRP3 genes in cancers of the brain and prostate.

Northern Blot analysis of mRNA from tumor samples, using full or partial RRP1 (SEQ ID NO: 1), RRP2 (SEQ ID NO:3), and RRP3 (SEQ ID NO:5) cDNA sequences as probes, can determine whether particular tumors overexpress RRP (Current Protocol in Molecular Biology, Eds. Asubel, et al., Wiley interscience, NY). Alternatively, the TaqMan® is used for analysis of RRP expression in tumor samples (PE Applied Biosystems).

Nucleic Acids of the Invention

A first aspect of the invention is a nucleic acid which encodes a human RRP3 as shown as SEQ ID NO:5. The DNA and RNA sequences of the invention can be single- or double-stranded. Thus, the term "isolated nucleic acid sequence", as used herein, includes the reverse complement, RNA equivalent, DNA or RNA single- or double-stranded sequences, and DNA/RNA hybrids of the sequence being described, unless otherwise indicated.

A part of the first aspect of the invention includes a fragment of a nucleic acid, such as a fragment that encodes a binding domain of one of the full-length sequences of the invention. Fragments of the RRP3 nucleic acid sequences can be used for a variety of purposes. As an example, interfering RNA (RNAi) fragments, particularly double-stranded (ds) RNAi, can be used to generate loss-of-function phenotypes; which can, in turn, be used, among other uses, to determine gene function. Methods relating to the use of RNAi to silence genes in C. elegans, Drosophila, plants, and humans are known in the art (Fire A, et al., Nature 391:806–811 (1998); Fire, A. Trends Genet. 15, 358–363 (1999); Sharp, P. A. RNA interference 2001. Genes Dev. 15, 485–490 (2001); Hammond, S. M., et al., Nature Rev. Genet. 2, 110–1119 (2001); Tuschl, T. Chem. Biochem. 2, 239–245 (2001); Hamilton, A. et al., Science 286, 950–952 (1999); Hammond, S. M., et al., Nature 404, 293–296 (2000); Zamore, P. D., et al., Cell 101, 25–33 (2000); Bernstein, E., et al., Nature 409, 363–366 (2001); Elbashir, S. M., et al., Genes Dev. 15, 188–200 (2001); WO0129058; WO9932619; Elbashir S M, et al., 2001 Nature 411:494–498).

Certain "antisense" fragments, i.e. that are reverse complements of portions of the coding and/or untranslated regions (e.g. 5' UTR) of SEQ ID NO:5 have utility in inhibiting the function of RRP3 proteins. The fragments are of length sufficient to specifically hybridize with the corresponding SEQ ID NO:5. The fragments consist of or comprise at least 12, preferably at least 24, more preferably at least 36, and more preferably at least 96 contiguous nucleotides of SEQ ID NO:5. When the fragments are flanked by other nucleic acid sequences, the total length of the combined nucleic acid sequence is less than 15 kb, preferably less than 10 kb or less than 5 kb, more preferably less than 2 kb, and in some cases, preferably less than 500 bases.

Additional preferred fragments of SEQ ID NO:5 encode extracellular or intracellular domains which are located at approximately nucleotides 248–598, 665–796, 862–870, 934–943, 1006–1138, 1201–1225, and 1289–1336. Preferred fragments may also include a binding domain or an RRP motif (e.g. PFAM 01694). These domains may be useful to locate the function and/or binding partners of a protein. For example, a nucleic acid that encodes an extracellular or intracellular domain of a protein may be used to screen for binding partners related to the protein.

The subject nucleic acid sequences may consist solely of SEQ ID NO:5 or fragments thereof. Alternatively, the subject nucleic acid sequences and fragments thereof may be joined to other components such as labels, peptides, agents that facilitate transport across cell membranes, hybridization-triggered cleavage agents or intercalating agents. The subject nucleic acid sequences and fragments thereof may also be joined to other nucleic acid sequences (i.e. they may comprise part of larger sequences) and are of synthetic/non-natural sequences and/or are isolated and/or are purified, i.e. unaccompanied by at least some of the material with which it is associated in its natural state. Preferably, the isolated nucleic acids constitute at least about 0.5%, and more preferably at least about 5% by weight of the total nucleic acid present in a given fraction, and are preferably recombinant, meaning that they comprise a non-natural sequence or a natural sequence joined to nucleotide (s) other than that which it is joined to on a natural chromosome.

Derivative nucleic acid sequences of RRP3 include sequences that hybridize to the nucleic acid sequence of SEQ ID NO:5. Various hybridization conditions are well-known to those skilled in the art (Current Protocol in Molecular Biology, supra). Specifically, stringent hybridization conditions may be employed: buffer comprising 30% formamide in 5×SSPE (0.18 M NaCl, 0.01 M NaPO4, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C.

The subject nucleic acids find a wide variety of applications including use as translatable transcripts, hybridization probes, PCR primers, diagnostic nucleic acids, etc.; use in detecting the presence of RRP3 genes and gene transcripts and in detecting or amplifying nucleic acids encoding additional RRP3 homologs and structural analogs. In diagnosis, RRP3 hybridization probes find use in identifying wild-type and mutant RRP3 alleles in clinical and laboratory samples. Mutant alleles are used to generate allele-specific oligonucleotide (ASO) probes for high-throughput clinical diagnoses. In therapy, therapeutic RRP3 nucleic acids are used to modulate cellular expression or intracellular concentration or availability of active RRP3.

As used herein, "percent (%) nucleic acid sequence identity" with respect to a subject sequence, or a specified portion of a subject sequence, is defined as the percentage of nucleotides in the candidate derivative nucleic acid sequence identical with the nucleotides in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410; http://blast.wustl.edu/blast/README.html; hereinafter referred to generally as "BLAST") with all the search parameters set to default values. Derivative RRP3 nucleic acid sequences usually have at least 70% sequence identity, preferably at least 80% sequence identity, more preferably at least 85% sequence identity, still more preferably at least 90% sequence identity, and most preferably at least 95% sequence identity with SEQ ID NO:5, or domain-encoding regions thereof.

In one preferred embodiment, the derivative nucleic acid encodes a polypeptide comprising a RRP3 amino acid sequence of SEQ ID NO:6, or a fragment or derivative thereof. A derivative RRP3 nucleic acid sequence, or fragment thereof, may comprise 100% sequence identity with SEQ ID NO:5, but be a derivative thereof in the sense that it has one or more modifications at the base or sugar moiety, or phosphate backbone. Examples of modifications are well known in the art (Bailey, Ullmann's Encyclopedia of Industrial Chemistry (1998), 6th ed. Wiley and Sons). Such derivatives may be used to provide modified stability or any other desired property.

More specific embodiments of preferred RRP3 protein fragments and derivatives are discussed below in connection with specific RRP3 proteins.

Proteins of the Invention

As a second aspect, the invention is drawn to RRP proteins of which comprise or consist of an amino acid sequence of SEQ ID NOs:4 or 6, or fragments or derivatives thereof. Compositions comprising these proteins may consist essentially of the RRP protein, fragments, or derivatives, or may comprise additional components (e.g. pharmaceutically acceptable carriers or excipients, culture media, etc.).

RRP protein derivatives typically share a certain degree of sequence identity or sequence similarity with SEQ ID NOs:4 or 6, or a fragment thereof. As used herein, "percent (%) amino acid sequence identity" with respect to a subject sequence, or a specified portion of a subject sequence, is defined as the percentage of amino acids in the candidate derivative amino acid sequence identical with the amino acid in the subject sequence (or specified portion thereof), after aligning the sequences and introducing gaps, if necessary to achieve the maximum percent sequence identity, as generated by BLAST (Altschul et al., supra) using the same parameters discussed above for derivative nucleic acid sequences. A % amino acid sequence identity value is determined by the number of matching identical amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids arginine, lysine and histidine; interchangeable acidic amino acids aspartic acid and glutamic acid; and interchangeable small amino acids alanine, serine, cysteine, threonine, and glycine.

In one preferred embodiment, an RRP protein derivative shares at least 80% sequence identity or similarity, preferably at least 85%, more preferably at least 90%, and most preferably at least 95% sequence identity or similarity with a contiguous stretch of at least 25 amino acids, preferably at least 50 amino acids, more preferably at least 100 amino acids, and in some cases, the entire length of SEQ ID NOs:4 or 6. In a preferred embodiment, the identity is shared with the RRP domain (PFAM 01694).

The fragment or derivative of the RRP protein is preferably "functionally active" meaning that the RRP protein derivative or fragment exhibits one or more functional activities associated with a full-length, wild-type RRP protein comprising the amino acid sequence of SEQ ID NOs:4 or 6. Preferably, a functionally active RRP fragment or derivative is one that displays one or more biological activities associated with RRP proteins. As one example, a fragment or derivative may have antigenicity such that it can be used in immunoassays, for immunization, for modulation of RRP activity, etc, as discussed further below regarding generation of antibodies to RRP proteins. For purposes herein, functionally active fragments also include those fragments that exhibit one or more structural features of an RRP, such as extracellular or intracellular domains. The functional activity of RRP proteins, derivatives and fragments can be assayed by various methods known to one skilled in the art (Current Protocols in Protein Science (1998) Coligan et al., eds., John Wiley & Sons, Inc., Somerset, N.J.).

RRP derivatives can be produced by various methods known in the art. The manipulations which result in their production can occur at the gene or protein level. For example, a cloned RRP gene sequence can be cleaved at appropriate sites with restriction endonuclease(s) (Wells et al., Philos. Trans. R. Soc. London SerA (1986) 317:415), followed by further enzymatic modification if desired, isolated, and ligated in vitro, and expressed to produce the desired derivative. Alternatively, an RRP gene can be mutated in vitro or in vivo, to create and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. (1986) 13:4331), use of TAB® linkers (available from Pharmacia and Upjohn, Kalamazoo, Mich.), etc.

At the protein level, manipulations include post translational modification, e.g. glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known technique (e.g. specific chemical cleavage by cyanogen bromide, trypsin, chymotrypsin, papain, V8 protease, NaBH$_4$, acetylation, formylation, oxidation, reduction, metabolic synthesis in the presence of tunicamycin, etc.). Derivative proteins can also be chemically synthesized by use of a peptide synthesizer, for example to introduce nonclassical amino acids or chemical amino acid analogs as substitutions or additions into the RRP protein sequence.

Chimeric or fusion proteins can be made comprising an RRP protein or fragment thereof (preferably comprising one or more structural or functional domains of the RRP protein) joined at its amino- or carboxy-terminus via a peptide bond to an amino acid sequence of a different protein. Chimeric proteins can be produced by any known method, including: recombinant expression of a nucleic acid encoding the protein (comprising a RRP-coding sequence joined in-frame to a coding sequence for a different protein); ligating the appropriate nucleic acid sequences encoding the desired amino acid sequences to each other in the proper coding frame, and expressing the chimeric product; and protein synthetic techniques, e.g. by use of a peptide synthesizer.

The subject RRP polypeptides also encompass minor deletion mutants, including N-, and/or C-terminal truncations. Such deletion mutants are readily screened for RRP competitive or dominant negative activity.

RRP Expression and Production

RRP polypeptides may be purified from cells that normally synthesize them, produced by recombinant technology from cultured cells, or synthesized in cell-free systems (e.g. Jermutus L, et al., Curr Opin Biotechnol. (1998) 9:534–48). A wide variety of molecular and biochemical methods are available for biochemical synthesis, molecular expression and purification of the subject compositions (Sambrook et al., Molecular Cloning, Cold Spring Harbor (1989), Current Protocols in Molecular Biology (supra)). Synthesized or recombinantly produced polypeptides are generated from polynucleotides that encode them. These may be naturally-encoding polynucleotides isolated with degenerate oligonucleotide primers and probes generated from the subject polypeptide sequences ("GCG" software, Genetics Computer Group, Inc, Madison Wis.), or polynucleotides optimized for selected expression systems made by back-translating the subject polypeptides according to computer algorithms (e.g. Holler et al., Gene (1993) 136: 323–328; Martin et al., Gene (1995) 154:150–166). In one embodiment, recombinant cells that express RRP under the control of a heterologous promoter are used in assays to screen for agents that modulate RRP function, as described further below.

RRP-Modulating Agents

The invention provides methods of identifying and making such modulating agents, and their use in diagnosis, therapy and pharmaceutical development. Chemical binding agents can be identified by screening of chemical libraries such as in vitro, cell-based and animal-based binding assays described further below, or otherwise known to those of skill in the art. Endogenous RRP-specific binding agents and other natural intracellular binding agents can be identified using one-, two- and three-hybrid screens. RRP-binding specificity may be assayed by TGFα processing (e.g. ability of the candidate RRP-specific binding agents to function as negative effectors in RRP-expressing cells), by binding equilibrium constants (usually at least about $10^7$ M$^{-1}$, preferably at least about $10^8$ M$^{-1}$, more preferably at least about $10^9$ M$^{-1}$), by immunogenicity (e.g. ability to elicit RRP specific antibody in a heterologous host such as a mouse, rat, goat or rabbit), etc.

The invention also provides RRP-modulating agents that act by inhibiting or enhancing RRP expression or directly or indirectly affect RRP binding activity. RRP-modulating agents include RRP mutant proteins (e.g. dominant negative mutants), RRP-specific antibodies, and chemical agents that specifically bind RRP. Preferred RRP-modulating agents specifically bind to RRP polypeptides and inhibit RRP function. RRP-specific binding agents may be evaluated by any convenient in vitro or in vivo assay for its molecular interaction with an RRP polypeptide. Preferably, the RRP polypeptide is from a human source (e.g. SEQ ID NOs:2, 4, or 6), but can be a homolog or ortholog thereof (e.g. with at least 80%, preferably 85%, more preferably 90%, and most preferably at least 95% sequence identity with SEQ ID NOs:2, 4, or 6). The binding agent may be endogenous, i.e. one normally implicated in RRP signal transduction such as TGFα, EGF, amphiregulin, heregulin, an RRP regulating protein, or another pathway regulator that directly modulates RRP activity or its localization. Alternatively, the binding agent may be exogenous, such as RRP-specific antibodies, T-cell antigen receptors (see, e.g Harlow and Lane (1988) Antibodies, A Laboratory Manual, Cold Spring Harbor Laboratory) or a chemical binding agent, such as a chemical agent identified by an assay of the present invention.

Specific binding agents such as antibodies and RRP-specific small molecules, as discussed further below, are useful in a variety of diagnostic and therapeutic applications, especially where disease or disease prognosis is associated with a pathway that involves RRP such as the EGFR pathway. Accordingly, the invention also provides methods for modulating the EGFR pathway in a cell comprising the step of modulating RRP activity.

RRP Specific Antibodies

Antibodies that specifically bind RRP proteins can be generated. The antibodies have therapeutic and diagnostic utilities, and uses in functional validation of RRP genes and proteins. For example, uses for antibodies include the detection of an RRP protein in a biological sample and the inhibition of RRP activity, for instance, to block the development of an oncogenic disorder. The antibodies can also be used in dissecting the portions of the RRP pathway responsible for various cellular responses and in the general processing and maturation of the RRP.

Antibodies that specifically bind RRP polypeptides can be generated using known methods. Preferably the antibody is specific to a mammalian RRP protein, and more preferably, a human RRP protein. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Antibodies may be generated against crude cell extracts of RRP or substantially purified fragments thereof. If RRP fragments are used, they preferably comprise at least 10, and more preferably, at least 20 contiguous amino acids of an intracellular or extracellular domain of RRP.

Polyclonal antibodies to the various RRP polypeptide and peptide fragments may be prepared. In a particular embodiment, the subject polypeptides provide RRP-specific antigens and/or immunogens that are coupled to carrier proteins, which stimulate their own immune response. For example, the subject polypeptides are covalently coupled to the keyhole limpet hemocyanin (KLH) carrier, and the conjugate is emulsified in Freund's complete adjuvant, which enhances the immune response. An appropriate immune system such as laboratory rabbits or mice are immunized according to conventional protocols and bled to recover the antibodies. The presence of RRP-specific antibodies is assayed by an appropriate assay such as a solid phase enzyme-linked immunosorbant assay (ELISA) using immobilized corresponding RRP polypeptides. Other assays, such as radioimmunoassays or fluorescent assays might also be used.

Monoclonal antibodies (mAbs) are homogenous, clonally derived, and bind with single antigenic determinants. When monoclonal antibodies (mAbs) are generated, they preferably have affinities of at least $10^8$ $M^{-1}$, and preferably $10^9$ $M^{-1}$ to $10^{10}$ $M^{-1}$, or stronger. Standard procedures for mAbs are known in the art (Harlow and Lane, Antibodies: A Laboratory Manual, CSH Laboratory (1988); Goding (1986) Monoclonal Antibodies: Principles and Practice (2d ed) Academic Press, New York; and U.S. Pat. Nos. 4,381,292, 4,451,570 and 4,618,577). Briefly, appropriate animals will be selected and the desired immunization protocol followed. After the appropriate period of time, the spleens of such animals are excised and individual spleen cells fused, typically, to immortalized myeloma cells under appropriate selection conditions. The cells are then clonally separated, and the supernatants of all clones tested by ELISA for their production of an antibody specific for the desired region of the antigen.

Chimeric antibodies specific to RRP polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851–6855; Neuberger et al., Nature (1984) 312:604–608; Takeda et al., Nature (1985) 31:452–454). Humanized antibodies, which are a form of chimeric antibodies, can be generated by grafting complementary-determining regions (CDRs) (Carlos, T. M., J. M. Harlan. 1994. Blood 84:2068–2101) of mouse antibodies into a background of human framework regions and constant regions by recombinant DNA technology (Riechmann L M, et al., 1988 Nature 323: 323–327). Humanized antibodies contain ~10% murine sequences and ~90% human sequences, and thus further reduce or eliminate immunogenicity, while retaining the antibody specificities (Co MS, and Queen C. 1991 Nature 351: 501–501; Morrison S L. 1992 Ann. Rev. Immun. 10:239–265). Humanized antibodies and methods of their production are well-known in the art (U.S. Pat. No. 5,530,101; U.S. Pat. No. 5,585,089; U.S. Pat. No. 5,693,762, and U.S. Pat. No. 6,180,370).

RRP-specific single chain antibodies, which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423–426; Huston et al., Proc. Natl. Acad. Sci. USA (1988) 85:5879–5883; and Ward et al., Nature (1989) 334:544–546).

Other suitable techniques for antibody production involve in vitro exposure of lymphocytes to the antigenic polypeptides or alternatively to selection of libraries of antibodies in phage or similar vectors (Huse et al., Science (1989) 246:1275–1281).

The antibodies of the present invention may be used with or without modification. Frequently, the polypeptides and antibodies will be labeled by joining, either covalently or non-covalently, a substance that provides for a detectable signal, or that is toxic to cells that express the targeted protein (Menard S, et al., Int J. Biol Markers (1989) 4:131–134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567).

Therapeutic Uses of the Antibodies

When used for anti-tumor therapy in a patient, the antibodies of the subject invention are administered to the patient in therapeutically effective amounts that eliminate or reduce the patient's tumor burden. They will normally be administered parenterally, when possible at the target cell site, or intravenously. The dose and dosage regimen will depend upon the nature of the cancer (primary or metastatic), its population, the target site, the characteristics of the particular immunotoxin (when used), e.g., its therapeutic index, and the patient's history. The amount of antibody administered will typically be in the range of approximately 0.1–10 mg/kg of patient weight. Treatment regimens using therapeutic antibodies are known in the art (e.g. U.S. Pat. No. 5,859,206).

As is known in the art, the selection of an appropriate antibody subclass for therapy will depend upon the nature of the tumor antigen. For example, an IgM may be preferred when the antigen is highly specific for the tumor target and rarely occurs on normal cells. However, the IgG subclass may be preferred when the tumor-associated antigen is also expressed in normal tissues, even at much lower levels. The binding of at least two IgG molecules in close proximity is required to activate complement, a serum protein that combines with antibodies to form a defense against cellular antigens. The normal tissues that express smaller amounts of the antigen and bind fewer IgG molecules may thus incur less complement-mediated damage. Furthermore, since IgGs are smaller than IgMs, they may more readily localize to tumor tissue.

Immune responses may assist in the delivery or efficacy of an anti-tumor treatment. There is evidence that complement activation leads to an inflammatory response and macrophage activation (Uananue and Benecerraf, Textbook of Immunology, 2nd Edition, Williams & Wilkins, p. 218 (1984)). Activated macrophages more preferentially destroy tumor cells than normal cells (Fidler and Poste, Springer Semin. Immunopathol. 5, 161 (1982)). Also, the increased vasodilation accompanying inflammation may increase the ability of anti-cancer agents, such as chemotherapeutic drugs or radiolabeled antibodies to localize in tumors. While a significant detriment of standard chemotherapy or radiation treatment is damage to healthy cells, the antigen-antibody combinations specified by this invention may circumvent many of the problems normally caused by the heterogeneity of tumor cell populations. Additionally, purified antigens (Hakomori, Ann. Rev. Immunol. (1984) 2:103) or the related anti-idiotypic antibodies (Nepom et al., Proc. Natl. Acad. Sci, (1985) 81:2864; Koprowski et al., Proc. Natl. Acad. Sci. (1984) 81:216) which recognize the hypervariance among the same epitopes in different individuals could be used to induce an active immune response in human cancer patients. Such a response includes the formation of antibodies capable of activating human complement and mediating antibody-dependent cell-mediated cytotoxicity and by such mechanisms cause tumor destruction.

Non-Antibody Modulators of RRP Function

The invention provides efficient methods of identifying non-antibody modulators of RRP function, and preferably chemical agents, e.g. lead compounds that can modulate RRP by gene expression, transcription, or cellular function. A wide variety of assays for transcriptional modulators or binding agents can be used, including labeled in vitro ligand binding assays, immunoassays, etc. (Harlow and Lane, Antibodies, supra; Knopfel et al., J. Med. Chem. (1995) 38:1417). The methods are amenable to automated, cost-effective high throughput screening of chemical libraries for lead compounds. Identified reagents can be used in the pharmaceutical industries for animal and human trials. Assays for binding agents include screens for compounds that modulate RRP interaction with a natural RRP binding target. The RRP polypeptide used in such assays may be fused to another polypeptide such as a peptide tag for detection or anchoring, etc. In a particular embodiment, the binding target is TGFα, or a portion thereof, which provides binding affinity and avidity to the subject RRP polypeptide conveniently measurable in the assay and preferably comparable to the intact TGFα. Candidate binding agents encompass numerous chemical classes. They are typically organic compounds, preferably small (e.g., preferably having a molecular weight of less than 10,000, more preferably less than 5,000, still most preferably less than 1,000, and most preferably less than 500), and are obtained from a wide variety of sources including libraries of synthetic or natural compounds. A variety of other reagents may also be included in the mixture such as salts, buffers, neutral proteins such as albumin, detergents, protease inhibitors, nuclease inhibitors, antimicrobial agents, etc. The resultant mixture is incubated under conditions whereby, but for the presence of the candidate pharmacological agent, the RRP polypeptide specifically binds the cellular binding target, portion or analog with a reference binding affinity. The mixture components can be added in any order that allow the requisite bindings, and incubations may be performed at any temperature that facilitates binding. Incubation periods are likewise selected for optimal binding but also minimized to facilitate rapid, high-throughput screening.

After incubation, any agent-biased binding between the RRP polypeptide and one or more binding targets is detected by any of a variety of methods depending on the nature of the product and other assay components, such as through optical or electron density, radiative emissions, nonradiative energy transfers, etc. or indirect detection with antibody conjugates, etc. A difference in the binding affinity of RRP to the target in the absence of the agent, as compared with the binding affinity in the presence of the agent indicates that the agent modulates the binding of the RRP to the RRP binding target, i.e. there is "agent-biased" binding. A difference, as used herein, is statistically significant and preferably represents at least a 50%, preferably at least 60%, more preferably 75%, and most preferably a 90% difference.

Compound Formulations

The compounds identified in the assays of the invention described herein are typically formulated in pharmaceutical compositions, for example, as composition that comprise other active ingredients, as in combination therapy, and/or suitable carriers or excipient(s). Techniques for formulation and administration of the compounds of the instant application may be found in "Remington's Pharmaceutical Sciences," Mack Publishing Co., Easton, Pa., latest edition.

Genetically Modified Animals

A preferred method of secondary validation of modulating agents is the use of animals and/or animal models, such as models of EGFR-related pathologies. Accordingly, the invention provides non-human animals that have been genetically modified to alter RRP expression. Preferably, the altered RRP expression results in a detectable phenotype, such as decreased or increased levels of cell proliferation, angiogenesis, or apoptosis compared to control non-human animals having normal RRP expression. The genetically modified animal may additionally have altered EGFR expression. Preferred genetically modified animals are mammals such as primates, rodents (preferably mice), cows, horses, goats, sheep, pigs, dogs and cats. Preferred non-mammalian species include Zebrafish, *C. elegan,* and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761–763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438–4442 (1985), U.S. Pat. Nos. 4,736,866 and 4,870,009, both by Leder et al., U.S. Pat. No. 4,873,191 by Wagner et al., U.S. Pat. No. 6,127,598, by German et al., and Hogan, B., Manipulating the Mouse Embryo, Cold Spring Harbor Laboratory Press, Cold Spring Harbor, N.Y., (1986); for particle bombardment see U.S. Pat. No. , 4,945,050, by Sandford et al.; for transgenic *Drosophila* see Rubin and Spradling, Science (1982) 218:348–53 and U.S. Pat. No. 4,670,388; for transgenic insects see Berghammer A. J. et al., A Universal Marker for Transgenic Insects (1999) Nature 402:370–371; for transgenic Zebrafish see Lin S., Transgenic Zebrafish, Methods Mol Biol. (2000); 136:375–3830); for microinjection procedures for fish, amphibian eggs and birds see Houdebine and Chourrout, Experientia (1991) 47:897–905; for transgenic rats see Hammer et al., Cell (1990) 63:1099–1112; and for culturing of embryonic stem (ES) cells and the subsequent production of transgenic animals by the introduction of DNA into ES cells using methods such as electroporation, calcium phosphate/DNA precipitation and direct injection see, for example, Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810–813; and PCT International Publication Nos. WO 97/07668 and WO 97/07669).

In one embodiment, the transgenic animal is a "knock-out" animal having a heterozygous or homozygous alteration in the sequence of an endogenous RRP gene that results in a decrease of RRP function, preferably such that RRP expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse RRP gene is used to construct a homologous recombination vector suitable for altering an endogenous RRP gene in the mouse genome. Detailed methodologies for homologous recombination in mice are available (see Capecchi, Science (1989) 244:1288–1292; Joyner et al., Nature (1989) 338:153–156). Procedures for the production of non-rodent transgenic mammals and other animals are also available (Houdebine and Chourrout, supra; Pursel et al., Science (1989) 244:1281–1288; Simms et al., Bio/Technology (1988) 6:179–183).

In another embodiment, the transgenic animal is a "knock-in" animal having an alteration in its genome that results in altered expression (e.g., increased (including ectopic) or decreased expression) of the RRP gene, e.g., by introduction of additional copies of RRP, or by operatively inserting a regulatory sequence that provides for altered expression of an endogenous copy of the RRP gene. Such regulatory sequences include inducible, tissue-specific, and constitutive promoters and enhancer elements. The knock-in can be homozygous or heterozygous.

Transgenic nonhumans animals can also be produced that contain selected systems allowing for regulated expression of the transgene. One example of such a system is the cre/loxP recombinase system of bacteriophage P1 (Lakso et al., PNAS (1992) 89:6232–6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of *Saccharomyces cerevisiae* (O'Gorman et al. (1991) Science 251:1351–1355; U.S. Pat. No. 5,654,182).

The genetically modified animals can be used in genetic studies to further elucidate the EGFR pathway, as animal models of disease and disorders implicating defective EGFR pathway function, and for in vivo testing of candidate therapeutic agents, such as those identified in the above-identified screens. The candidate therapeutic agents are administered to a genetically modified animal having altered RRP function and phenotypic changes are compared with appropriate control animals such as genetically modified animals that receive placebo treatment, and/or animals with unaltered RRP expression that receive candidate therapeutic agent.

Gene Therapy

RRP sequences of the invention will also be useful in gene therapy (reviewed in Miller, Nature 357:455–460, 1992; Badiavas E V and Falanga V., J. Dermatol (2001) April; 28(4):175–92; Maron et al. Surg Oncol Clin N Am (2001) April; 10(2):449–60; and Mulligan, Science 260:926–931 (1993)). Recent advances in gene therapy have resulted in positive results.

In one preferred embodiment, an expression vector containing a RRP coding sequence, such as a dominant negative form, is inserted into cells. The cells are grown in vitro and then infused into patients. In another preferred embodiment, a DNA segment containing a heterologous promoter or enhancer is transferred into cells containing an endogenous gene encoding RRP of the invention in such a manner that the promoter/enhancer segment enhances expression of the endogenous RRP gene (for example, the promoter segment is transferred to the cell such that it becomes directly linked to the endogenous RRP gene).

The gene therapy may involve the use of an adenovirus containing RRP cDNA targeted to a tumor, systemic RRP increase by implantation of engineered cells, injection with RRP encoding virus, or injection of naked RRP DNA into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction, may be used to inhibit an abnormal, deleterious signal transduction event.

Expression vectors derived from viruses such as retroviruses, vaccinia virus, adenovirus, adeno-associ-ated virus, herpes viruses, several RNA viruses, or bovine papilloma virus, may be used for delivery of nucleotide sequences (e.g, cDNA) encod-ing recombinant RRP of the invention protein into the targeted cell population (e.g, tumor cells). Methods which are well known to those skilled in the art can be used to construct recombinant viral vectors containing coding sequences (Maniatis et al., Molecular Cloning: A Laboratory Manual, Cold Spring Harbor Laboratory, N.Y., 1989; Ausubel et al., Current Protocols in Molecular Biology, Greene Publishing Associates and Wiley Interscience, N.Y., 1989). Alternatively, recombinant nucleic acid molecules encoding protein sequences can be used as naked DNA or in a reconstituted system e.g., liposomes or other lipid systems for delivery to target cells (e.g, Felgner et al., Nature 337:387–8, 1989). Several other methods for the direct transfer of plasmid DNA into cells exist for use in human gene therapy and involve targeting the DNA to receptors on cells by complexing the plasmid DNA to proteins (Miller, supra).

In its simplest form, gene transfer can be performed by simply injecting minute amounts of DNA into the nucleus of a cell, through a process of microinjection (Capecchi, Cell 22:479–88,1980). Once recombinant genes are introduced into a cell, they can be recognized by the cell's normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis (Chen et al., Mol. Cell Biol. 7:2745–52, 1987); electroporation, wherein cells are exposed to large voltage pulses to introduce holes into the membrane (Chu et al., Nucleic Acids Res. 15:1311 –26, 1987); lipofection/ liposome fusion, wherein DNA is packaged into lipophilic vesicles which fuse with a target cell (Felgner et al., Proc. Natl. Acad. Sci. USA. 84:7413–7417, 1987); and particle bombardment using DNA bound to small projectiles (Yang et al., Proc. Natl. Acad. Sci. 87:9568–9572, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene (Curiel et al., Am. J. Respir. Cell. Mol. Biol., 6:247–52, 1992).

Gene transfer, the process of introducing a foreign nucleic acid molecule into a cell is commonly performed to enable the expression of a particular product encoded by the gene. The product may include a protein, polypeptide, antisense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cyto-plasm from the plasma membrane or endosome. Expression may require, in addition, movement of the nucleic acid into the nucleus of the cell and binding to appropriate nuclear factors for transcription. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a RRP polypeptide is provided in which the nucleic acid sequence is expressed only in specific tissue. Methods of achieving tissue-specific gene expression are set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement, supplying a nucleic acid sequence which is capable of being expressed in vivo in an animal and thereby providing or augmenting the function of an endogenous gene which is missing or defective in the animal is set forth.

The following experimental section and examples are offered by way of illustration and not by way of limitation.

EXAMPLES, PROTOCOLS AND EXPERIMENTAL PROCEDURES

I. High-Throughput In Vitro Fluorescence Polarization Assay

Fluorescently-labeled RRP peptide/TGF-α polypeptide are added to each well of a 96-well microtiter plate, along with a test compound of choice in a test buffer (10 mM HEPES, 10 mM NaCl, 6 mM magnesium chloride, pH 7.6). The amount of fluorescence polarization is then determined by using a Fluorolite FPM-2 Fluorescence Polarization Microtiter System (Dynatech Laboratories, Inc).

II. Conformational Sensor—ELISA Format Assay

Various combinations of Glutathione-S-transferase/TGF-α polypeptide fusion protein and biotinylated RRP are added to each well of a microtiter plate (Reacti-Bind Streptavidin-Coated, White Polystyrene Plates (#15118B), which have been blocked by Super-Blocking Reagent from Pierce) in assay buffer(0.01M HEPES, 0.15M NaCl, 0.002M $MgCl_2$). Test compounds are then added to each well, and incubated at room temperature for 1 hour. Anti-GST, rabbit and anti-rabbit antibodies are then added to each well and incubated on ice for 1 hour. Plates are then washed with water, diluted Supersignal substrate is added to each well, and chemiluminescence is then measured.

III. High-Throughput In Vitro Binding Assay.

$^{33}P$-labeled RRP peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a compound of interest to the wells of a Neutralite-avidin coated assay plate, and incubated at 25° C. for 1 hour. Biotinylated TGF-α polypeptide is then added to each well, and incubated for 1 hour. Reactions are stopped by washing with PBS, and counted in a scintillation counter. Controls for the assays, located on each plate are non-biotinylated TGF-α polypeptide.

IV. Expression Analysis

All cell lines used in the following experiments are NCI (National Cancer Institute) lines,a nd are available from ATCC (American Type Culture Collection, Manassas, Va. 20110-2209). Normal and tumor tissues were obtained from Impath, UC Davis, Clontech, Stratagene, and Ambion.

TaqMan® (PE Applied Biosystems) was used for analysis of human RRP1, RRP2, and RRP3 expression in normal human tissues, matched colon tumor and normal samples, pooled tumor tissues from breast, ovary, lung, prostate, and liver cancer, compared to normal and tumor cell lines. All procedures were carried out according to manufacturer's protocols.

Normal human tissue samples. Ubiquitous expression of all rhomboids was observed in all tissues examined, with highest levels of expression in the brain. Higher expression in the spinal cord was also observed for RRP3.

Matched tumor and normal samples. Higher expression in colon tumor relative to normal matched tissue was seen in 8 out of 18 tumors for RRP1, 1 out of 19 tumors for RRP2, and 4 out of 18 tumors for RRP3. In addition, RRP1 displayed higher expression in pooled tumor tissues from breast, ovarian, lung, prostate and liver cancer compared to normal. RRP2 was overexpressed in one pool of breast tumor and two pools of ovarian tissues compared to matched normal tissues. RRP3 expression was increased in one pool of lung tumor tissue compared to matched normal tissue.

Tumor cell lines. Lymphoma, lung, breast, and colon tumor cell lines were used for these studies. RRP1 was expressed in all tumor lines, with highest expression levels in colon cancer; RRP2 showed increased expression only in breast cancer lines; and RRP3 expression was increased slightly in breast and colon cancer lines, but increased significantly in lung cancer lines.

V. Cell Biology and Functional Characterization

RRP Localization. In *Drosophila*, rhomboid is a cell surface protein. However, localization of human RRPs has not happened to date. Furthermore, in humans, it is not known whether each of the termini of the rhomboids is intracellular or extracellular. To answer these questions, RRP1 was subcloned into pcDNA expression vector (Invitrogen) in frame with myc-his tag at the c-terminus, according to manufacturer's protocols. The resulting expression vector was transiently transfected using Lipofectamine Plus reagent (Life technologies) into human embryonic kidney HEK-293 cells. Immunofluorescence staining using anti-myc antibody was then carried out on the cells to localize RRP1. Results of these experiments indicated that RRP1 is expressed at the cell surface. Furthermore, permeabilized (0.1% triton in PBS) and non-permeabilized cells show the same staining pattern, indicating that the c-terminus of the protein is outside, and the N-terminus, inside. RRP2 and RRP3 are also subcloned and tagged at the c-terminus for localization of each protein, and also to assess the direction of the protein ends in each case.

Involvement of RRP in EGFR signaling pathway. While *Drosophila* rhomboid is essential in the EGFR pathway, the function of human RRPs have not been assessed to date. To assess the role of human RRPs in the EGFR signaling pathway, RRP1 was stably transfected using CaPO4 transfection kit (Clontech) into Hela cells, which have endogenous EGFR activity. Pooled stable cells were then examined in the following assays.

EGFR Activation as Measured by Tyrosine Phosphorylation

Hela cells overexpressing RRP1 and parental Hela cells were tested for EGFR tyrosine phosphorylation by immunoblot against anti-phosphotyrosine using anti-phosphotyrosine antibody (Upstate Biotechnology). Cells overexpressing RRP1 demonstrated up to two-fold increase in EGFR tyrosine phosphorylation as compared to parental Hela controls.

EGFR Expression in Cells Overexpressing RRP1.

Expression of EGFR was increased when tested by immunoblot using anti-EGFR antibody against direct cell lysates in cells overexpressing RRP1. Furthermore, expression of EGFR was also increased in tumor samples overexpressing RRP1, by TaqMan® analysis. The correlation of both in-vitro and in-vivo results for concordant overexpression of EGFR and RRP1 is quite significant, and provides a tool for assessing the functional relationship of the two proteins in any tumor sample or cell line.

Cell Proliferation and Migration.

Hela cells overexpressing RRP1 demonstrate a two-fold increase in cell proliferation compared to Hela parental cells as measured by Procheck (Intergen) and AlamarBlue (Biosource International) chemiluminescent assays. In addition, Fluroblok (BD Biosource) analysis showed a slight increase in motility in cells overexpressing RRP1 compared to Hela parental cells.

Taken together, these results demonstrate a strong functional conservation of rhomboids across evolution. Furthermore, increased RRP1 expression in tumor samples and cell lines, concurrent increased expression of EGFR, and increased proliferation and motility of cells expressing RRP1 suggest involvement of RRP1 in various cancers. RRP1 expression levels can thus be used to screen for tumors with defective EGFR pathways, to identify tumors amenable to treatment with the compounds and antibodies identified by the methods of the present invention. Same aforementioned experiments are performed with RRP2 and RRP3 to assess their involvement in the EGFR signaling pathway.

RRP1 binding target. In *Drosophila,* rhomboid transforms Spitz (homolog of human TGF-α) from a membrane-bound to a secreted form, and thus triggers and upregulates the DER (*Drosophila* EGFR) pathway. No such function has been shown for human rhomboids. HEK293 cells were transiently co-transfected with RRP1 and TM-TGF-α (transmembrane-bound TGF), then immunoprecipitated with anti-myc antibody (for RRP1) and immunoblotted with anti-TGF-α. Cells transfected with vector alone, RRP1 alone, or TM-TGF-α alone were used as controls. A band corresponding to the size of TGF-α was recognized by anti-TGF-α antibody, while no bands were detected in the control lanes. This data indicates that RRP1 physically interacts with TGF-α. The same experiments are performed with RRP2 and RRP3 to determine their binding partners.

Antibodies against human rhomboids. A peptide antibody, SEQ ID NO: 7, and referred to as peptide 1, was made against the N-terminus of RRP1. This antibody displayed strong affinity for denatured RRP1, such as in cells fixed with formalin or proteins on western blots. In addition, staining pattern remained the same when permeabilized cells were co-stained with anti-myc antibodies (for the c-terminus of RRP1) and peptide 1, suggesting that Peptide 1 does recognize RRP1. Furthermore, the cells were significantly immunostained only when they were permeabilized, suggesting that the N-terminus of RRP1 is inside the cells. This result correlates with the previous staining pattern using anti-myc antibody for the C-terminus.

RRP1 protein expression in tumors was examined by Immunohistochemistry (IHC) using peptide 1. Positive staining on epithelial cells of colon adenocarcinoma tissue sections were observed as compared to background staining in preimmune serum, suggesting the antibody is specific for its target, RRP1, in colon cancer cells. Moreover, increased staining of colorectal adenocarcinomas was observed compared to matched normal tissues using peptide 1 antibody. Taken together, these results suggest that peptide 1 antibody is a powerful tool to assess expression levels of RRP1 in tumor samples. Antibodies are also produces against RRP2 and RRP3, to assess their expression levels in tumors.

One skilled in the art would readily appreciate that the present invention is well adapted to carry out the objects and obtain the ends and advantages mentioned above, as well as those inherent therein. The molecular complexes and methods, procedures, treatments, molecules, specific compounds described herein are presently representative of preferred embodiments, are exemplary, and are not intended as limitations on the scope of the invention. It will readily be apparent to one skilled in the art that varying substitutions and modifications may be made to the invention disclosed herein without departing from the scope and spirit of the invention.

All patents and publications mentioned in the specification are indicative of the levels of skill to which the invention pertains. All patents and publications are herein incorporated by reference to the same extent as if each individual publication was specifically and individually indicated to be incorporated by reference.

Other embodiments are within the following claims:

What is claimed is:

1. A method for in vitro detection of Rhomboid-related protein 1 (RRPI) of SEQ ID NO:2 in a tumor cell comprising contacting said cell with an anti-RRP1 antibody and detecting binding of the antibody to RRP1.

2. The method of claim 1 wherein said tumor cell is in a tissue sample.

3. The method of claim 1 wherein said tumor cell is selected from the group consisting of lymphoma, lung, breast, and colon tumor cells.

4. The method of claim 2 wherein said tissue is selected from the group consisting of breast, ovary, lung, prostate, and liver tissue.

5. The method of claim 2 wherein said tissue sample is from colon.

* * * * *

SEQUENCE LISTING

<160> NUMBER OF SEQ ID NOS: 7

<210> SEQ ID NO 1
<211> LENGTH: 1559
<212> TYPE: DNA
<213> ORGANISM: Homo sapiens

<400> SEQUENCE: 1
cttggacctt ggccctcgct ttccaggatg ggtagggtgg aagacggggg aacaactgag    60

-continued

```
gagctggagg actgggaccc aggcaccagt gccctgccag ctcctgggat caagcagggt      120
cccagggaac agacaggcac ggggcccctg tcccaaaagt gctgggagcc tgagcctgat      180
gctcccagcc agcctggccc agcccttttgg tccaggggtc gggcccgcac tcaggccttg     240
gctggcggct cctcactgca gcagctggac cccgagaaca caggcttcat cggtgcggac      300
accttcactg gcctggtgca cagccatgag ctgcccctgg accggccaa gctggacatg       360 ctggtggccc tggctcagag caacgagcag ggccaggtct gctaccagga gctggtggac      420
ctgatcagca gcaagcgctc cagcagtttc aagcgggcca ttgctaacgg acagcgggca      480
ctgccccggg acgggccgct ggatgagcca ggcctaggtg tctacaagcg gtttgtgcgt     540
tacgtggcct acgagatcct gccttgtgag gtggaccgcc gctggtactt ctaccgtcac      600
cgcagctgcc acccccccgt gttcatggcc tcggtcactc ttgcccagat catcgtgttc      660
ctgtgttacg gggcccgcct caacaagtgg gtgctgcaga cctaccaccc cgagtacatg      720
aagagccccc ttgtgtacca ccccgggcac cgtgcccgcg cctggcgctt cctcacctac      780
atgttcatgc acgttgggct ggagcagctg gggttcaacg ccctcctgca gctgatgatc      840
ggggtgcccc tggagatggt gcacggcctg ctccgcatca gcctgctcta cctggcaggc      900
gtgctggcag gctccctaac cgtctccatc accgacatgc gggccccggt ggtgggaggc      960
tccggcgggg tctacgccct gtgctcggca cacctggcca acgttgtcat gaactgggct     1020
gggatgagat gtccctacaa gttgctgagg atggtgctgg ccttggtgtg catgagctcc     1080
gaggtgggcc gggccgtgtg gctgcgcttc tccccgccgc tgcccgcctc gggcccacag     1140
cccagcttca tggcgcacct ggcaggcgcg gtggtggggg tgagcatggg cctgaccatc     1200
ctgcggagct acgaggagcg cctgcgggac cagtgcggct ggtgggtggt gctgctggcc     1260
tacggcacct tcctgctctt cgccgtcttc tggaacgtct tcgcctacga cctgctgggc     1320
gcccacatcc cccaccgcc ctgaccggct acctgaggct gcacaggcca gggctcgggc     1380
atgtggtggc cgcccaccag gggccttcac gtctgccctt tgtgaacgga cgtctcaggg     1440
ctgctgtgcc ccttgggtgt gggtggcctc aaaggaggcc ctgtcccagc acccacccc    1500 ccactcccag gacttgcggt ctgagccttt ttggataatt aataaatatt ttacacagc     1559
```

<210> SEQ ID NO 2
<211> LENGTH: 438
<212> TYPE: PRT
<213> ORGANISM: Homo sapiens

<400> SEQUENCE: 2

```
Met Gly Arg Val Glu Asp Gly Gly Thr Thr Glu Glu Leu Glu Asp Trp
1               5                   10                  15

Asp Pro Gly Thr Ser Ala Leu Pro Ala Pro Gly Ile Lys Gln Gly Pro
            20                  25                  30

Arg Glu Gln Thr Gly Thr Gly Pro Leu Ser Gln Lys Cys Trp Glu Pro
        35                  40                  45

Glu Pro Asp Ala Pro Ser Gln Pro Gly Pro Ala Leu Trp Ser Arg Gly
    50                  55                  60

Arg Ala Arg Thr Gln Ala Leu Ala Gly Gly Ser Ser Leu Gln Gln Leu
65                  70                  75                  80

Asp Pro Glu Asn Thr Gly Phe Ile Gly Ala Asp Thr Phe Thr Gly Leu
                85                  90                  95

Val His Ser His Glu Leu Pro Leu Asp Pro Ala Lys Leu Asp Met Leu
            100                 105                 110
```

```
Val Ala Leu Ala Gln Ser Asn Glu Gln Gly Gln Val Cys Tyr Gln Glu
            115                 120                 125

Leu Val Asp Leu Ile Ser Ser Lys Arg Ser Ser Phe Lys Arg Ala
    130                 135                 140

Ile Ala Asn Gly Gln Arg Ala Leu Pro Arg Asp Gly Pro Leu Asp Glu
145                 150                 155                 160

Pro Gly Leu Gly Val Tyr Lys Arg Phe Val Arg Tyr Val Ala Tyr Glu
                165                 170                 175

Ile Leu Pro Cys Glu Val Asp Arg Arg Trp Tyr Phe Tyr Arg His Arg
                180                 185                 190

Ser Cys Pro Pro Val Phe Met Ala Ser Val Thr Leu Ala Gln Ile
            195                 200                 205

Ile Val Phe Leu Cys Tyr Gly Ala Arg Leu Asn Lys Trp Val Leu Gln
                210                 215                 220

Thr Tyr His Pro Glu Tyr Met Lys Ser Pro Leu Val Tyr His Pro Gly
225                 230                 235                 240

His Arg Ala Arg Ala Trp Arg Phe Leu Thr Tyr Met Phe Met His Val
            245                 250                 255

Gly Leu Glu Gln Leu Gly Phe Asn Ala Leu Leu Gln Leu Met Ile Gly
                260                 265                 270

Val Pro Leu Glu Met Val His Gly Leu Arg Ile Ser Leu Leu Tyr
    275                 280                 285

Leu Ala Gly Val Leu Ala Gly Ser Leu Thr Val Ser Ile Thr Asp Met
    290                 295                 300

Arg Ala Pro Val Val Gly Gly Ser Gly Gly Val Tyr Ala Leu Cys Ser
305                 310                 315                 320

Ala His Leu Ala Asn Val Val Met Asn Trp Ala Gly Met Arg Cys Pro
                325                 330                 335

Tyr Lys Leu Leu Arg Met Val Leu Ala Leu Val Cys Met Ser Ser Glu
                340                 345                 350

Val Gly Arg Ala Val Trp Leu Arg Phe Ser Pro Pro Leu Pro Ala Ser
    355                 360                 365

Gly Pro Gln Pro Ser Phe Met Ala His Leu Ala Gly Ala Val Val Gly
    370                 375                 380

Val Ser Met Gly Leu Thr Ile Leu Arg Ser Tyr Glu Glu Arg Leu Arg
385                 390                 395                 400

Asp Gln Cys Gly Trp Trp Val Val Leu Leu Ala Tyr Gly Thr Phe Leu
                405                 410                 415

Leu Phe Ala Val Phe Trp Asn Val Phe Ala Tyr Asp Leu Leu Gly Ala
            420                 425                 430

His Ile Pro Pro Pro
            435

<210> SEQ ID NO 3
<211> LENGTH: 1224
<212> TYPE: DNA
<213> ORGANISM: Homo sapiens

<400> SEQUENCE: 3
gggccattta ggaggtttag atcattttga tcatcttcag ctgtcttctc ttcacataca    60
ggaaaggcct tggaaagcag tcgttgcgcc agacagccca gggaagagcg gcagcctgag   120
gacctagggc cacctgctgt tccctgggat tcatgtcctt ctggggagga gggaggaccc   180
aggacaatgg ctgctgttca tgatctggag atggagagca tgaatctgaa tatggggaga   240
```

-continued

```
gagatgaaag aagagctgga ggaagaggag aaaatgagag aggatggggg aggtaaagat      300
cgggccaaga gtaaaaaggt ccacaggatt gtctcaaaat ggatgctgcc cgaaaagtcc      360
cgaggaacat acttggagag agctaactgc ttcccgcctc ccgtgttcat catctccatc      420
agcctggccg agctggcagt gtttatttac tatgctgtgt ggaagcctca gaaacagtgg      480
atcacgttgg acacaggcat cttggagagt ccctttatct acagtcctga aagagggag       540
gaagcctgga ggtttatctc atacatgctg gtacatgctg gagttcagca catcttgggg      600
aatctttgta tgcagcttgt tttgggtatt cccttggaaa tggtccacaa aggcctccgt      660
gtggggctgg tgtacctggc aggagtgatt gcagggtccc ttgccagctc catctttgac      720
ccactcagat atcttgtggg agcttcagga ggagtctatg ctctgatggg aggctatttt      780
atgaatgttc tggtgaattt tcaagaaatg attcctgcct ttggaattt cagactgctg      840
atcatcatcc tgataattgt gttggacatg ggatttgctc tctatagaag gttctttgtt      900
cctgaagatg ggtctccggt gtcttttgca gctcacattg caggtggatt tgctggaatg      960
tccattggct acacggtgtt tagctgcttt gataaagcac tgctgaaaga tccaaggttt     1020
tggatagcaa ttgctgcata tttagcttgt gtcttatttg ctgtgttttt caacattttc     1080
ctatctccag caaactgacc tgcccctatt gtaagtcaat taataaaaag agccatctgg     1140
aggaaataaa aaaaaaagga agactctatg aagaaacaga gaagtctcag aaaaggctaa     1200
caattttaga tagagaacaa aggg                                            1224
```

<210> SEQ ID NO 4
<211> LENGTH: 303
<212> TYPE: PRT
<213> ORGANISM: Homo sapiens

<400> SEQUENCE: 4

```
Met Ala Ala Val His Asp Leu Glu Met Glu Ser Met Asn Leu Asn Met
1               5                   10                  15

Gly Arg Glu Met Lys Glu Glu Leu Glu Glu Glu Lys Met Arg Glu
            20                  25                  30

Asp Gly Gly Gly Lys Asp Arg Ala Lys Ser Lys Lys Val His Arg Ile
        35                  40                  45

Val Ser Lys Trp Met Leu Pro Glu Lys Ser Arg Gly Thr Tyr Leu Glu
    50                  55                  60

Arg Ala Asn Cys Phe Pro Pro Val Phe Ile Ile Ser Ile Ser Leu
65                  70                  75                  80

Ala Glu Leu Ala Val Phe Ile Tyr Tyr Ala Val Trp Lys Pro Gln Lys
                85                  90                  95

Gln Trp Ile Thr Leu Asp Thr Gly Ile Leu Glu Ser Pro Phe Ile Tyr
            100                 105                 110

Ser Pro Glu Lys Arg Glu Glu Ala Trp Arg Phe Ile Ser Tyr Met Leu
        115                 120                 125

Val His Ala Gly Val Gln His Ile Leu Gly Asn Leu Cys Met Gln Leu
    130                 135                 140

Val Leu Gly Ile Pro Leu Glu Met Val His Lys Gly Leu Arg Val Gly
145                 150                 155                 160

Leu Val Tyr Leu Ala Gly Val Ile Ala Gly Ser Leu Ala Ser Ser Ile
                165                 170                 175

Phe Asp Pro Leu Arg Tyr Leu Val Gly Ala Ser Gly Gly Val Tyr Ala
            180                 185                 190
```

```
Leu Met Gly Gly Tyr Phe Met Asn Val Leu Asn Phe Gln Glu Met
            195                 200                 205

Ile Pro Ala Phe Gly Ile Phe Arg Leu Leu Ile Ile Leu Ile Ile
            210                 215                 220

Val Leu Asp Met Gly Phe Ala Leu Tyr Arg Arg Phe Val Pro Glu
225                 230                 235                 240

Asp Gly Ser Pro Val Ser Phe Ala Ala His Ile Ala Gly Phe Ala
                245                 250                 255

Gly Met Ser Ile Gly Tyr Thr Val Phe Ser Cys Phe Asp Lys Ala Leu
                260                 265                 270

Leu Lys Asp Pro Arg Phe Trp Ile Ala Ile Ala Ala Tyr Leu Ala Cys
            275                 280                 285

Val Leu Phe Ala Val Phe Phe Asn Ile Phe Leu Ser Pro Ala Asn
            290                 295                 300
```

<210> SEQ ID NO 5
<211> LENGTH: 1376
<212> TYPE: DNA
<213> ORGANISM: Homo sapiens

<400> SEQUENCE: 5

```
ctgaactgat gaggttttca tgggaaatca gtgcctgtct gttcatctga acacccacta      60
gttattcatc caacaaatct tgattgagtg ctgataatgc caggctctgt gctaagtacc     120
ggggataagt tgtgataccg acccgcgagg cgccgcggtc caaggaggag caaaagcag      180
acagacatca gtgtgggctg gaggcccaga ggtctggaca gaacagaggg ttccgtgaga     240
acaggccatg gctgagtttg accctgggaa cacaggctac attagcacag gcaagttccg     300
gagtcttctg gagagccaca gctccaagct ggacccgcac aaaagggagg tcctcctggc     360
tcttgccgac agccacgcgg atgggcagat cggctaccag gattttgtca gcctagtgag     420
caacaagcgt tccaacagct ccgccaagc catcctgcag gcaaccgca ggctaagcag       480
caaggccctg ctggaggaga aggggctgag cctctcgcag cgacttatcc gccatgtggc     540
ctatgagacc ctgccccggg aaattgaccg caagtggtac tatgacagct acacctgctg     600
cccccccacc tggttcatga tcacagtcac gctgctggag gttgcctttt tcctctacaa     660
tggggtgtca ctaggtcaat ttgtactgca ggtaactcat ccacgttact gaagaactc     720
cctggtttac cacccacagc tgcgagcaca ggtttggcgc tacctgacat acatcttcat     780
gcatgcaggg atagaacacc tgggactcaa tgtggtgctg cagctgctgg tgggggtgcc     840
cctggagatg gtgcatggag ccacccgaat tgggcttgtc tacgtggccg tgttgtggc     900
agggtccttg gcagtgtctg tggctgacat gaccgctcca gtcgtgggct cttctggagg     960
ggtgtatgct ctcgtctctg cccatctggc caacattgtc atgaactggt caggcatgaa    1020
gtgccagttc aagctgctgc ggatggctgt ggcccttatc tgtatgagca tggagtttgg    1080
gcgggccgtg tggctccgct ccacccgtc ggcctatccc ccgtgccctc acccaagctt     1140
tgtggcgcac ttgggtggcg tggccgtggg catcaccctg gcgtggtgg tcctgaggaa    1200
ctacgagcag aggctccagg accagtcact gtggtggatt tttgtggcca tgtacaccgt    1260
cttcgtgctg ttcgctgtct tctggaacat cttgcctac accctgctgg acttaaagct     1320
gccgcctccc ccctgagggc tggaggccca aggtcgggga ggggagggaa aagcag         1376
```

<210> SEQ ID NO 6
<211> LENGTH: 362
<212> TYPE: PRT

<213> ORGANISM: Homo sapiens

<400> SEQUENCE: 6

```
Met Ala Glu Phe Asp Pro Gly Asn Thr Gly Tyr Ile Ser Thr Gly Lys
1               5                   10                  15
Phe Arg Ser Leu Leu Glu Ser His Ser Ser Lys Leu Asp Pro His Lys
            20                  25                  30
Arg Glu Val Leu Leu Ala Leu Ala Asp Ser His Ala Asp Gly Gln Ile
        35                  40                  45
Gly Tyr Gln Asp Phe Val Ser Leu Val Ser Asn Lys Arg Ser Asn Ser
    50                  55                  60
Phe Arg Gln Ala Ile Leu Gln Gly Asn Arg Arg Leu Ser Ser Lys Ala
65                  70                  75                  80
Leu Leu Glu Glu Lys Gly Leu Ser Leu Ser Gln Arg Leu Ile Arg His
                85                  90                  95
Val Ala Tyr Glu Thr Leu Pro Arg Glu Ile Asp Arg Lys Trp Tyr Tyr
            100                 105                 110
Asp Ser Tyr Thr Cys Cys Pro Pro Trp Phe Met Ile Thr Val Thr
        115                 120                 125
Leu Leu Glu Val Ala Phe Phe Leu Tyr Asn Gly Val Ser Leu Gly Gln
    130                 135                 140
Phe Val Leu Gln Val Thr His Pro Arg Tyr Leu Lys Asn Ser Leu Val
145                 150                 155                 160
Tyr His Pro Gln Leu Arg Ala Gln Val Trp Arg Tyr Leu Thr Tyr Ile
                165                 170                 175
Phe Met His Ala Gly Ile Glu His Leu Gly Leu Asn Val Val Leu Gln
            180                 185                 190
Leu Leu Val Gly Val Pro Leu Glu Met Val His Gly Ala Thr Arg Ile
        195                 200                 205
Gly Leu Val Tyr Val Ala Gly Val Val Ala Gly Ser Leu Ala Val Ser
    210                 215                 220
Val Ala Asp Met Thr Ala Pro Val Val Gly Ser Ser Gly Val Tyr
225                 230                 235                 240
Ala Leu Val Ser Ala His Leu Ala Asn Ile Val Met Asn Trp Ser Gly
                245                 250                 255
Met Lys Cys Gln Phe Lys Leu Leu Arg Met Ala Val Ala Leu Ile Cys
            260                 265                 270
Met Ser Met Glu Phe Gly Arg Ala Val Trp Leu Arg Phe His Pro Ser
        275                 280                 285
Ala Tyr Pro Pro Cys Pro His Pro Ser Phe Val Ala His Leu Gly Gly
    290                 295                 300
Val Ala Val Gly Ile Thr Leu Gly Val Val Val Leu Arg Asn Tyr Glu
305                 310                 315                 320
Gln Arg Leu Gln Asp Gln Ser Leu Trp Trp Ile Phe Val Ala Met Tyr
                325                 330                 335
Thr Val Phe Val Leu Phe Ala Val Phe Trp Asn Ile Phe Ala Tyr Thr
            340                 345                 350
Leu Leu Asp Leu Lys Leu Pro Pro Pro
        355                 360
```

<210> SEQ ID NO 7
<211> LENGTH: 19
<212> TYPE: PRT
<213> ORGANISM: Homo sapiens

-continued

```
<400> SEQUENCE: 7

Met Gly Arg Val Glu Asp Gly Gly Thr Thr Glu Glu Leu Glu Asp Trp
1               5                   10                  15

Asp Pro Gly
```